(12) United States Patent
Oldfield

(10) Patent No.: US 6,550,475 B1
(45) Date of Patent: Apr. 22, 2003

(54) ENDOTRACHEAL TUBE FOR SELECTIVE BRONCHIAL OCCLUSION

(75) Inventor: Geoffrey Stewart Oldfield, Whitebridge (AU)

(73) Assignee: Oldfield Family Holdings Pty. Limited, New South Wales (AU)

( * ) Notice: Subject to any disclaimer, the term of this patent is extended or adjusted under 35 U.S.C. 154(b) by 0 days.

(21) Appl. No.: 09/646,070

(22) PCT Filed: Mar. 11, 1999

(86) PCT No.: PCT/AU99/00150

§ 371 (c)(1),
(2), (4) Date: Sep. 11, 2000

(87) PCT Pub. No.: WO99/45990

PCT Pub. Date: Sep. 16, 1999

(30) Foreign Application Priority Data

Mar. 11, 1998 (AU) .............................................. PP2294

(51) Int. Cl.[7] ............................................ A61M 16/00
(52) U.S. Cl. .............................. 128/200.26; 128/207.15
(58) Field of Search ...................... 128/200.26, 207.14, 128/207.15; 604/96.01, 101.03

(56) References Cited

U.S. PATENT DOCUMENTS

| 2,175,726 A | * | 10/1939 | Gebauer | 604/101.03 |
|---|---|---|---|---|
| 2,210,744 A | * | 8/1940 | Winder | 128/207.15 |
| 3,884,242 A | * | 5/1975 | Bazell et al. | 128/207.15 |
| 4,230,108 A | * | 10/1980 | Young | 604/101.03 |
| 4,248,221 A | * | 2/1981 | Winnard | 604/101.03 |
| 4,327,720 A | * | 5/1982 | Bronson et al. | 128/207.15 |
| 4,453,545 A | * | 6/1984 | Inoue | 128/207.15 |
| 4,688,568 A | * | 8/1987 | Frass et al. | 128/207.15 |
| 4,705,502 A | * | 11/1987 | Patel | 604/101.03 |
| 4,819,664 A | * | 4/1989 | Nazari | 128/207.15 |
| 4,846,153 A | * | 7/1989 | Berci | 128/207.15 |
| 4,850,371 A | * | 7/1989 | Broadhurst et al. | 128/207.15 |
| 4,976,692 A | * | 12/1990 | Atad | 604/101.03 |
| 5,315,992 A | * | 5/1994 | Dalton | 604/101.03 |
| 5,499,625 A | * | 3/1996 | Frass et al. | 128/207.15 |
| 5,562,608 A | * | 10/1996 | Sekins et al. | 128/207.15 |

FOREIGN PATENT DOCUMENTS

| EP | 0 665 029 A2 | 1/1994 |
|---|---|---|
| GB | 2 168 256 A | 11/1984 |
| GB | 2 298 580 A | 2/1995 |

\* cited by examiner

*Primary Examiner*—Aaron J. Lewis
(74) *Attorney, Agent, or Firm*—Abelman, Frayne & Schwab

(57) ABSTRACT

An endotracheal tube (1) for selective bronchial occlusion for use in medical and surgical procedures in hospitals, and for on-site post-trauma medical stabilisation procedures, where it is often necessary to intubate the lungs with a view to isolating and occluding one lung and ventilating the other lung, the endotracheal tube (1) having a central channel (5) extending throughout its entire length with an opening at each of opposed distal (3) and proximal (4) ends thereof, the opening at the proximal end of the tube being adapted for connection to a ventilation device and the opening at the distal end comprising a first or distal air vent for venting air into the lungs, the bronchial/tracheal tube having separate spaced apart distal and proximal peripherally inflatable portions (6 and 7) at the distal end of the tube and at a proximal location relative thereto, respectively, and a second or proximal air vent opening (8) in the sidewall of that portion of the tube extending between the distal and proximal inflatable portions (6 and 7) wherein the distal inflatable portion (6) is inflatable both radially outwardly (as at 9) adapted to seal against the surrounding bronchus and radially inwardly (as at 10) to seal against itself to occlude the lumen of the tube (5) and wherein the proximal inflatable portion (7) is inflatable radially outwardly (as at 11) adapted to seal against the surrounding bronchial tube.

9 Claims, 1 Drawing Sheet

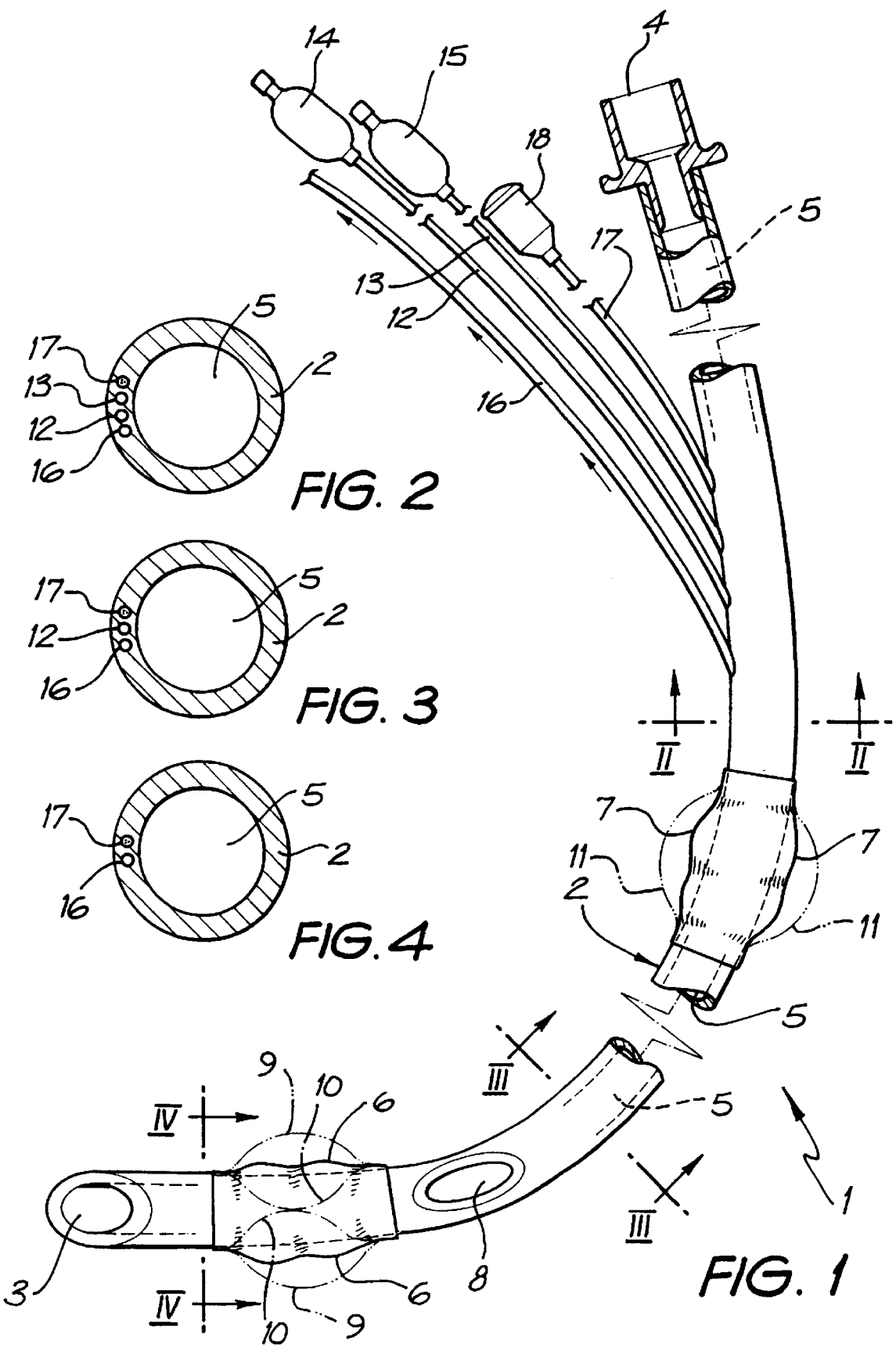

ENDOTRACHEAL TUBE FOR SELECTIVE BRONCHIAL OCCLUSION

TECHNICAL FIELD

The present invention relates to an improved endotracheal tube for selective bronchial occlusion for use in medical and surgical procedures in hospitals, and for on-site post-trauma medical stabilisation procedures.

BACKGROUND ART

In the event of damage to a lung, such as a collapsed lung following some form of trauma, it is often necessary to intubate the lungs with a view to isolating and occluding the damaged lung and ventilating the other lung.

Present devices and procedures for achieving this end are, in general, complex and require a high level of training and skill for accurate and effective placement. For example, with some patients, it may take the anaesthetist or surgeon up to one hour to occlude a collapsed lung and to ensure correct placement and intubation of the remaining functioning lung. Quite often anaesthetists lack the training or skills to ensure correct lung intubation/occlusion, and this procedure is left to the surgeon to perform.

In the case of paramedics, such as ambulance personnel, instigating primary stabilisation and treatment of traumatised patients at, for example, the scene of an accident, such paramedics lack the skills to correctly intubate and ventilate a patient with a damaged lung using existing medical equipment and procedures.

DISCLOSURE OF THE INVENTION

It is an object of this invention to provide an improved endotracheal tube for medical intubation which goes at least some way towards overcoming or at least minimising the prior art problems or limitations outlined above, and for providing a clear alternative choice for use by medical personnel.

It is another object of this invention to provide an endotracheal tube for medical intubation which provides for selective bronchial occlusion and ventilation of the lungs.

It is a further object of this invention to provide an endotracheal tube including means for easier or simpler selection of, and placement in, left or right bronchii.

It is yet another object of this invention to provide an improved endotracheal tube for selective bronchial occlusion/placement which is relatively simple to operate, and is suitable for use by both medical and paramedical personnel with minimal training and/or supervision.

These and other objects of the present invention will become more apparent from the following descriptions and drawings.

According to one aspect of the present invention, there is provided an endotracheal tube for selective bronchial occlusion and/or placement for lung ventilation of a patient, comprising an elongate, flexible bronchial/tracheal tube having a central channel or lumen extending throughout its entire length with an opening at each of opposed distal and proximal ends thereof, the opening at the proximal end of the tube being adapted for connection to a ventilation device and the opening at the distal end comprising a first or distal air vent for venting air into the lungs of a patient, said bronchial/tracheal tube having separate spaced apart distal and proximal peripherally inflatable portions at the distal end of the tube and at a proximal location relative thereto, respectively, and a second or proximal air vent opening in the sidewall of that portion of the tube extending between said distal and proximal inflatable portions thereof, wherein in situ said distal inflatable portion is inflatable both radially outwardly adapted to seal against the surrounding bronchus connected to one of the lungs and radially inwardly to seal against itself to occlude the lumen of the tube and thereby effectively occlude the lung, wherein said proximal inflatable portion is inflatable radially outwardly adapted to seal against the surrounding trachea of the patient, and whereby an airway to the patient's other lung is maintained via the said second or proximal air vent opening.

Ideally, the endotracheal tube comprises separate means for inflating the distal and proximal peripherally inflatable portions thereof, as well as separate fibre optic and suction means operative at the distal end of the tube to assist with placement of the tube into the left or right bronchii and or for draining air or fluids from the lung.

BRIEF DESCRIPTION OF THE ACCOMPANYING DRAWINGS

The invention will now be further described with reference to the accompanying drawings relating to one possible non-limiting embodiment of the invention. In the drawings:

FIG. 1 is a partially cut-away elevation of an endotracheal tube according to this embodiment of the invention;

FIG. 2 is a cross-sectional view of the tube of FIG. 1 taken along the line II—II of FIG. 1;

FIG. 3 is a further cross-sectional view of the tube of FIG. 1 taken along the line III—III of FIG. 1; and FIG. 4 represents another cross-sectional view of the tube of FIG. 1 taken along the line IV—IV of FIG. 1.

BEST MODE OF CARRYING OUT THE INVENTION

According to the embodiment as illustrated in FIG. 1, the endotracheal tube 1 comprises an elongate flexible bronchial/tracheal tube 2, having an open distal end 3 and an open proximal end 4 joined by an elongate central channel or lumen 5.

The endotracheal tube 1 has separate spaced-apart distal and proximal peripherally inflatable portions, 6 and 7 respectively, towards the distal end 3 of the tube, with an opening 8 in the peripheral sidewall of the tube. The distal inflatable portion 6 is inflatable peripherally both radially outwardly (as shown at 9) and radially inwardly (as at 10). The proximal inflatable portion 7 is inflatable peripherally radially outwardly only (as shown at 11).

Separate inflation means 12 and 13 are provided for inflation of the distal balloon 6 and the proximal balloon 7, respectively, comprising in each case elongate tubing extending externally from points adjacent the proximal end 4 of the endotracheal tube 1 and then peripherally and longitudinally within the sidewall of the tube 1, best seen in cross-section in FIGS. 2, 3 and 4, towards the inflatable balloons 6 and 7. An inflatable bladder (14 and 15), with a one-way non-return valve, is provided at the proximal ends of each tube 12 and 13, respectively. Each of inflatable balloons 6 and 7, is adapted to be inflated in use as and when required by attachment of a syringe at the bladder end 14 and 15 of the tubing 12 and 13 and injecting a predetermined quantity of air. Inflation of the balloons 6 and 7, in vivo, is indicated by inflation of the corresponding bladders 14 and 15, respectively.

Optionally, but preferably, a distal end suction tube 16 is provided for draining air or fluid from the lungs insitu. Likewise, it is preferred that the endotracheal tube includes re-useable fibre optic means 17, extending from the distal end 3 to the proximal end 4, to assist with placement of the tube 1 insitu. The inclusion of the tubes 12, 13, 16 and 17 in the peripheral sidewall of the bronchial/tracheal tube 2 is best demonstrated in the cross-sections thereof at positions II—II, III—III and IV—IV, as illustrated in FIGS. 2, 3 and 4, respectively.

The components of the endotracheal tube are fabricated from plastics materials which are conventionally used in medical and surgical applications.

In use, the endotracheal tube 1 is guided into the bronchus of the lung to be occluded for, say, surgical repair (e.g. the right lung) by means of the optical fibre viewing device 18 which provides visual direction or guidance of the distal end 3 of the endotracheal tube via optic fibre 17. When the distal end of the tube is correctly located in the bronchus of the right lung, the distal balloon 6 is inflated by injecting air via a syringe into the bladder end 14 of the elongate tube 12. Inflation of the bladder 14 indicates that the balloon 6 is inflated insitu, thus occluding the bronchus to the right lung. Air and secretions from the right lung can be drained therefrom by means of suction tube 16.

Inflation of balloon 7 by means of air injected via bladder 15 and tubing 13 results in occlusion of the bronchial tube surrounding the inflated balloon 7. The left lung can then be ventilated via the ventilation opening 8 in the sidewall of the endotracheal tube 1 which is in operative communication via lumen 5 with the ventilation means at the proximal end 4 of the tube. The inflated balloons 6 and 7 isolate those sections of the bronchial tube below balloon 6 and above balloon 7, completely occluding the right lung but allowing the left lung to work normally. Surgical repair of the occluded right lung is now possible.

The endotracheal tube is removed by first deflating the balloons 6 and 7 by releasing air from the bladder ends 14 and 15, and then withdrawing the endotracheal tube.

Although an exemplary embodiment of the present invention has been described and illustrated, it will be apparent to those having ordinary skill in the art that a number of changes, modifications or alterations to the invention described herein may be made, none of which depart from the spirit of the present invention. All such changes, modifications and alterations should therefore be seen as being within the scope of the present invention.

It should be appreciated that the present invention provides a substantial advance in endotracheal tubes for selective bronchial occlusion, providing all of the hereindescribed advantages without incurring any relative disadvantages.

What is claimed is:

1. A method of selective bronchial occlusion for lung ventilation of a patient wherein a first one of the patient's lungs is completely occluded and the second one of the patient's lungs remains in operable communication with an external ventilation device, said method comprising the steps of:

inserting an elongate, flexible bronchial/tracheal tube into the bronchus of the first lung, the tube having:
   a central lumen extending throughout the tube's entire length with an opening at each of opposed distal and proximal ends of the tube, the opening at the proximal end of the tube being adapted for connection to the external ventilation device, separate spaced apart distal and proximal peripherally inflatable portions at the distal end of the tube and at respective proximal locations relative to the distal end, a portion of the tube extending between the distal and proximal inflatable portions thereof having a sidewall, wherein the distal inflatable portion is inflatable both radially outwardly and radially inwardly to seal against itself, and wherein the proximal inflatable portion is inflatable radially outwardly, and a proximal air vent opening in the sidewall;

positioning the tube in the bronchus such that the distal inflatable portion is in the bronchus of the first lung, the tube being sized such that when the distal inflatable portion is positioned in the bronchus of the first lung, the proximal inflatable portion is positioned in the trachea of the patient above the bronchus of the second lung;

inflating the distal inflatable portion both radially outwardly to seal against the surrounding bronchus of the first lung and radially inwardly to seal against itself to occlude the lumen of the tube and thereby effectively occlude the first lung; and inflating the proximal inflatable portion radially outwardly to seal against the surrounding trachea of the patient, whereby an airway from the ventilation device to the patient's second lung is maintained via the proximal air vent opening.

2. The method of claim 1, wherein the distal and proximal inflatable portions of the tube are separately inflatable.

3. The method of claim 2, wherein said inflating steps occur separately and in either order.

4. The method of claim 2, wherein the tube further includes fiber optic means operative at the distal end of the tube for providing an image of the surroundings of the distal end to the proximal end, wherein said inserting and positioning steps include the step of using the image to assist in the correct insertion and positioning of the tube.

5. The method of claim 2, wherein the distal and proximal inflatable portions are each operatively connected to inflatable bladders fitted with respective one-way non-return valves.

6. The method of claim 2, wherein the tube further includes suction means operative at the distal end of the tube for draining air and/or fluid from the first lung.

7. The method of claim 1, wherein the tube further includes fiber optic means operative at the distal end of the tube for providing an image of the surroundings of the distal end to the proximal end, wherein said inserting and positioning steps include the step of using the image to assist in the correct insertion and positioning of the tube.

8. The method of claim 1, wherein the distal and proximal inflatable portions are each operatively connected to inflatable bladders fitted with respective one-way non-return valves.

9. The method of claim 1, wherein the tube further includes suction means operative at the distal end of the tube for draining air and/or fluid from the first lung.

* * * * *